United States Patent [19]

Oishi et al.

[11] Patent Number: 4,946,720
[45] Date of Patent: Aug. 7, 1990

[54] CONTAINERS FOR FILTHY MATTER

[75] Inventors: Tsukasa Oishi, Muko; Toshio Marui, Ogaki, both of Japan

[73] Assignees: Nippon Gohsei Kagaku Kogyo Kabushiki Kaisha, Osaka; Nichigo Film Kabushiki Kaisha, Ogaki, both of Japan

[21] Appl. No.: 284,631

[22] Filed: Dec. 15, 1988

[30] Foreign Application Priority Data

Dec. 17, 1987 [JP] Japan ................... 62-320565

[51] Int. Cl.⁵ .................. A61F 5/44; B65D 30/08
[52] U.S. Cl. .................... 428/35.4; 428/286; 428/522; 604/332
[58] Field of Search ............... 525/61; 428/35.4, 286, 428/520, 522; 604/332

[56] References Cited

U.S. PATENT DOCUMENTS

| | | | |
|---|---|---|---|
| 4,619,849 | 10/1986 | Anzawa et al. | 428/35.7 |
| 4,713,296 | 12/1987 | Aoyama et al. | 525/61 |
| 4,824,904 | 4/1989 | Aoyama et al. | 525/60 |

FOREIGN PATENT DOCUMENTS

| | | |
|---|---|---|
| 155408 | 9/1984 | Japan . |
| 60-1246 | 1/1985 | Japan . |
| 60-122527 | 7/1985 | Japan . |

Primary Examiner—James Seidleck
Attorney, Agent, or Firm—Armstrong, Nikaido, Marmelstein, Kubovcik & Murray

[57] ABSTRACT

A container for filthy matter particularly suited for use as a bag for collecting waste matter discharged through the artifical anus is essentially made of a single-layer or multilayer packaging material comprising an oxyalkylene group-containing vinyl alcohol copolymer film layer.

4 Claims, 2 Drawing Sheets

CONTAINERS FOR FILTHY MATTER

BACKGROUND OF THE INVENTION

This invention relates to containers for filthy waste matter, in particular bags for collecting excreta from the artificial anus, which have good flexibility and odor-retaining property and can be thrown into the flush toilet bowl without causing troubles.

Immediately after operative treatment of diseases of tubular or cavitary organs, such as ileum, transverse colon, descending colon, sigmoid colon and anal fistula, a minute opening (stoma), generally called an artificial anus, is sometimes formed on the body surface for discharge of filthy waste matter, such as fecal matter, pus or body fluid, therethrough. Not only immediately after operations but also during convalescence and even after return to work, the artificial anus is retained in many instances.

Bags for collecting the waste matter excreted from the artificial anus are called ostomy bags, colostomy bags, ileostomy bags and so forth depending of the tubular or cavitary organ to which the stoma is connected.

As to the construction of bags of this kind, various proposals have so far been made, as mentioned below.

Japanese Kokai Jitsuyo-Shinan Koho (unexamined utility model application publication) No. 142119/80 discloses bags for artificial anus which have an adsorbent paper/synthetic resin film structure, with an excessive amount of an adsorbent contained in the adsorbent as incorporated therein on the occasion of paper making.

A Japanese patent application filed under PTC and laid open under Kohyo No. 501631/82 discloses bags chiefly intended for medical use which have a structure such that a vapor barrier layer, such as a vinylidene chloride-vinyl chloride copolymer layer, lies between two layers made of a blend of a chlorinated polyolefin and an olefin polymer. In the relevant specification, mention is made, either as the prior art bags or bags for comparison, of bags for medical use which respectively have the following structures: polyethylene film, plasticized polyvinyl chloride film, a plasticized polyvinylidene chloride film, polyethylene/ethylene-vinyl acetate copolymer laminate, ethylene-vinyl acetate copolymer/polyvinylidene chloride/ethylene-vinyl acetate copolymer laminate, and polyethylene/ethylene-vinyl acetate copolymer/polyvinylidene chloride/ethylene-vinyl acetate copolymer/polyethylene laminate, among others.

Japanese Kokai Tokkyo Koho (unexamined patent application publication) No. 1246/85 discloses non-sound-producing films for the manufacture of ostomy bags which comprise either a layer of a blend of an ethylene-vinyl acetate copolymer and an elastic polyolefin or two layers of said blend and a gas/odor barrier layer of a vinylidene chloride copolymer, an ethylene-vinyl alcohol copolymer, a vinylidene fluoride-vinyl fluoride copolymer, a polyamide or the like as interposed between said two layers.

Japanese Kokai Tokkyo Koho No. 122527/85 discloses bags for excreta from the human body which are made of a 3-hydroxybutyrate polymer film or a laminate derived therefrom. As films usable for lamination to said film, there are mentioned water-soluble polymer films, such as polyvinyl alcohol films and polyethylene oxide films.

Japanese Kokai Jitsuyo-Shinan Koho No. 175248/85 discloses films for bags to be attached to an artificial anus which are produced by three-layer coextrusion of a blend of a saponified ethylene-vinyl acetate copolymer and a partially saponified ethylene-vinyl acetate copolymer (as middle layer) and an ethylene-(meth)acrylic ester copolymer (as sandwiching layers).

Japanese Kokai Tokkyo Koho No. 31151/86 discloses bags for receiving feces from the artificial anus which comprise a deodorizing coagulant disposed on the bag bottom and in the tubular section, where a readily water-soluble paper species is used.

Bags currently in practical use for collecting filthy waste matter excreted from the artificial anus have a three-layer construction of ethylene vinyl-acetate copolymer (inside layer)/polyvinylidene chloride/ethylenevinyl acetate copolymer (outside layer) or a four-layer construction derived from said three-layer construction by further lamination of a nonwoven fabric or a net-like structure.

Japanese Kokai Tokkyo Koho No. 155408/84 (the applicant being the same as in the present application), which is citable in connection with the present invention, discloses a method of producing modified polyvinyl alcohol which comprises saponifying a copolymer of an oxyalkylene group-containing unsaturated monomer and vinyl acetate. However, no mentioned is made therein of bags for collecting filthy matter excreted from the artificial anus.

Bags for collecting filthy matter discharged through the artificial anus are required to have, among others, the following properties:

(1) The filthy matter collected can be prevented from leaking from them (water resistance);

(2) No odor can leak out while they are worne (odor barrier property);

(3) They will not produce any sound so that others can never become aware of the fact of wearing thereof (non-sound-producing property or flexibility);

(4) They can be thrown into the flush toilet bowl without causing stopping up of the flush line (disposability in flush toilet);

(5) Their feel and touch are never unpleasant to wearers (acceptability in touch).

The bags disclosed in the above-cited references cannot meet all the requirements mentioned above. Even those bags currently in practical use which have an ethylene-vinyl acetate copolymer/polyvinylidene chloride/ethylene-vinyl acetate copolymer three-layer structure or a four-layer structure derived therefrom by further lamination of a nonwoven fabric or a net-like material may possibly cause stopping up of the flush line if they are thrown into the flush toilet bowl, although they are fairly satisfactory in respect of water resistance, odor barrier property, flexibility and feel and touch.

It is no doubt that artificial anus bearers are increasing in number year by year. The number of those artificial anus bearers that have returned to work is also increasing. Under these circumstances, it has earnestly waited for the advent of bags capable of meeting all the requirements mentioned above.

Accordingly, it is an object of the invention to provide bags which can meet such requirements as mentioned above.

SUMMARY OF THE INVENTION

The invention provides a container for filthy matter which is essentially made of a single-layer or multilayer packaging material comprising an oxyalkylene group-containing vinyl alcohol copolymer film layer.

BRIEF DESCRIPTION OF THE DRAWINGS

In the accompanying drawings.

Figure 1:
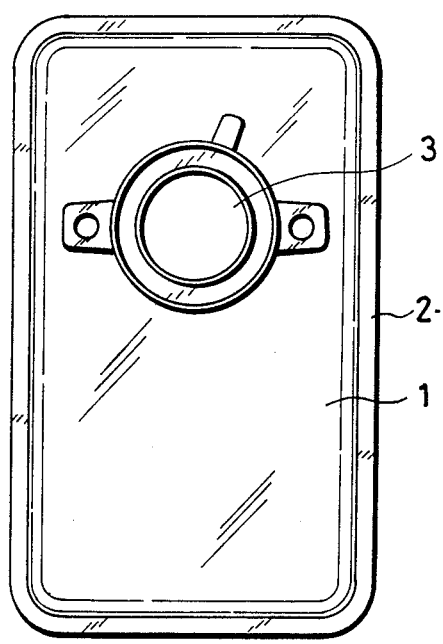
FIG. 1 is a plan view of an example of the container for filthy matter as provided by the invention.

In the figures, the reference numeral 1 indicates a single-layer or multilayer packaging material comprising an oxyalkylene group-containing vinyl alcohol copolymer film layer, and 1a, 1b and 1c denote the oxyalkylene group-containing vinyl alcohol copolymer film layer, another polymer film layer and a nonwoven fabric, respectively. The numeral 2 indicates a sealed portion, and 3 an opening portion.

DETAILED DESCRIPTION OF THE INVENTION

The oxyalkylene group-containing vinyl alcohol copolymer to be used in accordance with the invention is preferably a saponification product derived from a copolymer of an ethylenically unsaturated monomer containing an oxyalkylene group of the formula

-[CHR-CHR'-O-]$_n$H wherein R and R' each independently is H or an alkyl group (in particular a methyl or ethyl group) and n is a positive integer, and vinyl acetate.

Specific examples of the oxyalkylene group-containing, ethylenically unsaturated monomer are polyoxyethylene (meth)acrylate, polyoxypropylene (meth)acrylate, polyoxyethylene (meth)acrylamide, polyoxypropylene (meth)acrylamide, polyoxyethylene (1-(meth)acrylamido-1,1-dimethylpropyl) ester, polyoxyethylene (meth)allyl ether, polyoxypropylene (meth)allyl ether, polyoxyethylene vinyl ether and polyoxypropylene vinyl ether. In each case, the number of moles of oxyalkylene units added, namely n, is about 1 to about 300, preferably about 5 to about 50. Among the examples given above, polyoxyethylene allyl ether is most practicable.

The oxyalkylene group-containing vinyl alcohol copolymer can be prepared by copolymerizing an oxyalkylene group-containing, ethylenically unsaturated monomer such as mentioned above and vinyl acetate and then saponifying the resulting copolymer in an alcohol, such as methanol, ethanol or butanol, in the presence of an alkali catalyst.

The degree of saponification of the vinyl acetate component should be at least 10 mole percent. Since, however, a higher degree of saponification is more advantageous for the utilization of the properties of the vinyl alcohol group, the degree of saponification should generally be not less than 50 mole percent, preferably not less than 70 mole percent, more preferably not less than 90 mole percent.

The oxyalkylene group-containing vinyl alcohol copolymer obtained by saponification should preferably have an oxyalkylene group content of 1 to 80 percent by weight, more preferably 2 to 60 percent by weight, most preferably 5 to 50 percent by weight. When said content is too small, the flexibility will be damaged upon heat treatment of the film and conversely, when said content is excessive, the odor barrier property of the vinyl alcohol-based copolymer will be decreased.

In carrying out the polymerization mentioned above, one or more other monomers may be present in an amount of not more than about 30 mole percent, for example one or more monomers selected from among vinyl esters other than vinyl acetate, alkyl vinyl ethers, alkyl allyl ethers, ethylenically unsaturated carboxylic acids, esters, salts and acid anhydrides of such acids, α-olefins, vinyl chloride and so forth.

In some instances, the oxyalkylene group-containing vinyl alcohol copolymer may also be prepared by reacting polyvinyl alcohol with an alkylene oxide or by graft polymerization of vinyl acetate on a polyoxyalkylene glycol followed by saponification of the polymerization product.

A film of such oxyalkylene group-containing vinyl alcohol copolymer can be produced, for example, by casting an aqueous solution of said polymer, by melt extruding the polymer under aqueous conditions, or by melt extruding the polymer.

The thus-obtained film as such is apt to have insufficient water resistance. Therefore, when the film is to be used alone as the unilayer packaging material or as the inside layer of the multilayer packaging material, the film should desirably be heat-treated at a temperature of about 120° to 260° C., preferably about 130° to 240° C., so that it can become such that it is soluble in water only at temperatures not lower than 55° C. and has a 10% Young's modulus value of not more than $2 \times 10^{3^3}$ kg/cm$^2$ as measured at 20° C. and 50% RH (relative humidity).

The lowest temperature at which the film is soluble in water is defined as a temperature at which the dissolution of a film specimen, 3 cm × 3 cm in size and 25 ± 2 μm in thickness, reaches not less than 99 percent by weight when said specimen is put in 2,000 ml of cold water in a beaker and the temperature is then immediately raised at a rate of 2° C. per minute.

The container for filthy matter according to the invention may be constructed with the above-mentioned oxyalkylene group-containing vinyl alcohol copolymer film layer alone. From the utility viewpoint, however, said container should desirably be constructed by using a multilayer packaging material consisting of at least two layers resulting from combination of said copolymer film layer with another polymer film layer, an entangled fiber layer or a thin metal layer.

Suitable as the polymer film layer to be combined with the specific copolymer layer are film layers of olefin-based polymers, such as polyethylene, ethylene-propylene copolymers, ethylene-vinyl acetate copolymers, ethylene-acrylic ester copolymers and ionomers because of their being flexible and having water resistance. Furthermore, film layers of polymers having gas barrier property, such as polyvinylidene chloride and ethylene-vinyl alcohol copolymers, as well as film layers of such polymers as polyvinyl chloride, polyesters, polyamides and polyurethanes may also be used.

As the entangled fiber layer, there may be mentioned nonwoven fabrics, woven fabrics, knitted fabrics, paper sheets and net-like structures, among others.

The thin metal layer is, for example, a vapor deposited metal layer or a metal foil layer.

Figure 2:
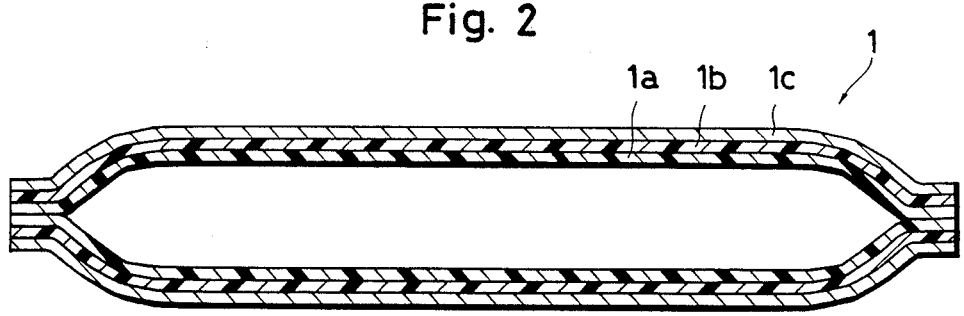
FIG. 2 and FIG. 3 each is a partial sectional view of an example of the container according to the invention, where the container is essentially made of a three-layer packaging material.
Figure 3:
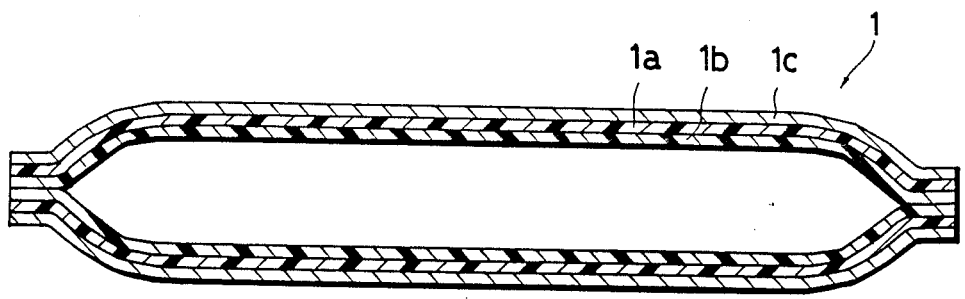

When the container is made of a multilayer packaging material consisting of at least three layers, a particularly preferred constitution thereof comprises, as shown in FIG. 2 and FIG. 3, said oxyalkylene group-containing vinyl alcohol copolymer layer as the container inside layer or the middle layer, a film layer of another polymer as the middle or inside layer, and a nonwoven fabric as the outside layer.

The multilayer packaging material can be produced, for example by lamination of films, coating of a layer with another layer, extrusion coating of a layer with another layer, coextrusion of layers and/or vapor deposition on a layer.

The container according to the invention generally has a bag-like shape. As desired, however, it may also have a bottle-like, tray-like, box-like or tube-like shape, for instance.

The container for filthy matter which has the above-mentioned constitution in accordance with the invention is particularly useful as a bag for collecting filthy matter extruded through the artificial anus. Furthermore, it can be used as a container for receiving various kinds of filthy matter as well as human or animal excrement.

The oxyalkylene group-containing vinyl alcohol copolymer film layer has the above-mentioned odor barrier property, flexibility and disposability in flush toilet at the same time.

Containers, for example bags, formed from a multilayer packaging material consisting of said layer and another polymer film layer, an entangled fiber layer and/or a thin metal layer can have disposability in flush toilet since, even when the other layer or layers are lacking in disposability in flush toilet, the oxyalkylene group-containing vinyl alcohol copolymer film layer with which said other layer or layers are laminated is swelled and deformed, so that the whole container can be deformed and thus become disposable in flush toilet.

Particularly when the inside or middle layer of the container is the oxyalkylene group-containing vinyl alcohol copolymer film layer, the middle or inside layer is another polymer film layer and the outside layer is a nonwoven fabric, the filthy matter collected and the odor thereof are prevented from leaking and the container as a whole is flexible and will not produce sound and therefore never allows others to become aware of the fact of wearing thereof. Such container is disposable in flush toilet and has favorable feel and touch because of the nonwoven fabric side coming into contact with the skin. Said container thus shows optimal performance characteristics as a bag for collecting filthy matter discharged from the artificial anus and therefore persons with an artificial anus can wear it without worrying about wearing it.

The following examples are further illustrative of the present invention.

EXAMPLE 1

Polyoxyethylene monoallyl ether with about 25 moles of oxyethylene added per mole thereof and vinyl acetate were copolymerized in methanol in the presence of azobisisobutyronitrile and the copolymer obtained was then saponified in the conventional manner.

Thus was obtained a polyoxyethylene group-containing vinyl alcohol copolymer having a degree of saponification of the vinyl acetate component of 99 mole percent and a polyoxyethylene content of 30 percent by weight. A 4% aqueous solution of the polymer had a viscosity of 10 cps as measured at 20° C.

A 25% (by weight) aqueous solution of this polymer was prepared, cast onto a stainless steel endless belt and passed through a drier to give a 25-$\mu$m-thick film.

This film was soluble in water at a temperature of 12° C. and had a 10% Young's modulus value of $0.4 \times 10^3$ kg/cm$^2$.

This film was then heat-treated in a hot air drier at a temperature of 170° C. for 1.5 minutes.

The heat-treated film thus obtained was soluble only at temperatures not lower than 59° C. and had a 10% Young's modulus value of $1.2 \times 10^3$ kg/cm$^2$. Thus it had water resistance and flexibility.

Bags of the type shown in FIG. 1 were made of this heat-treated single-layer film and evaluated for their performance characteristics.

EXAMPLE 2

The heat-treated film obtained in Example 1 was laminated on one side thereof with a 25-$\mu$m-thick low density polyethylene film by means of an adhesive. Bags of the type shown in FIG. 1 were made of the thus-obtained laminate with the polyethylene film layer as the outside layer.

EXAMPLE 3

The heat-treated film obtained in Example 1 was provided on one side thereof with a 10-$\mu$m-thick polyvinylidene chloride coating layer and further a nonwoven fabric having a weight of 20 g/m$^2$ was laminated with the composite (on the coating layer). Bags of the type shown in FIG. 1 were made of the thus-obtained three-layer composite with the nonwoven fabric layer serving as the outside layer.

EXAMPLE 4

The heat-treated film obtained in Example 1 was laminated on one side thereof with a 30-$\mu$m-thick ethylene-vinyl acetate copolymer (ethylene content 70 mole percent) film, followed by further lamination of a nonwoven fabric having a weight of 20 g/m$^2$. Bags of the type shown in FIG. 1 were made of the resultant composite with the nonwoven fabric side directed outward.

EXAMPLE 5

The heat-treated film obtained in Example 1 was laminated on one side thereof with a 30-$\mu$m-thick ethylene-vinyl acetate copolymer (ethylene conent 70 mole percent) film, followed by further lamination of a nonwoven fabric weighing 20 g/m$^2$ on the other side of said heat-treated film. Bags of the type shown in FIG. 1 were made of the resultant composite.

EXAMPLE 6

The heat-treated film obtained in Example 1 was laminated on one side thereof with an aluminum-deposited polyester film with the vapor deposition side faced with the heat-treated film, followed by further lamination of a nonwoven fabric having a weight of 20 g/m$^2$ thereon. Bags of the type shown in FIG. 1 were made of the resultant composite with the nonwoven fabric layer as the outside layer.

EXAMPLE 7

Polyoxypropylene monomethacrylamide (about 15 moles of oxypropylene added) and vinyl acetate were copolymerized in methanol in the presence of azobisisobutyronitrile and the copolymer obtained was then saponified in the conventional manner.

Thus was obtained a polyoxypropylene group-containing vinyl alcohol copolymer having a degree of saponification of the vinyl acetate component of 99 mole percent and a polyoxypropylene group content of 30 percent by weight.

A-25-μm-thick film was produced from an aqueous solution of this polymer by the casting method and then heat-treated in a hot air drier maintained at a temperature of 170° C. for 3 minutes.

The film after the heat treatment was soluble in water only at temperatures not lower than 62° C. and had a 10% Young's modulus value of $1.8 \times 10^3$ kg/cm$^2$, hence it had water resistance and flexibility.

Bags of the type shown in FIG. 1 were made of this heat-treated film in the same manner as in Example 3 and evaluated for their performance characteristics.

EXAMPLE 8

Polyoxyethylenepolyoxypropylene monoacrylate (about 10 moles of polyoxyethylene and about 10 moles of polyoxypropylene added) and vinyl acetate were copolymerized in methanol in the presence of azobisisobutyronitrile and the copolymer obtained was then saponified in the conventional manner.

Thus was obtained a polyoxyethylenepolyoxypropylene group-containing vinyl alcohol copolymer having a degree of saponification of the vinyl acetate component of 99 mole percent, a polyoxyethylene content of 15 percent by weight and a polyoxypropylene content of 15 percent by weight.

A 25-μm-thick film was produced from an aqueous solution of this polymer by the casting method and then heat-treated in a hot air drier maintained at a temperature of 170° C. for 3 minutes.

The film after the above heat treatment was soluble in water only at temperatures not lower than 60° C. and had a 10% Young's modulus value of $1.3 \times 10^3$ kg/cm$^2$. Thus it had water resistance and flexibility.

Bags of the type shown in FIG. 1 were made of this heat-treated film in the same manner as in Example 1 and evaluated for their performance characteristics.

COMPARATIVE EXAMPLE 1

A 25-μm-thick film was produced from polyvinyl alcohol having a saponification degree of 99 mole percent and a 4% aqueous solution viscosity of 10 cps/20° C. by the casting method.

This film was soluble in water at temperatures not lower than 65° C. and had a 10% Young's modulus value of $3.9 \times 10^3$ kg/cm$^2$.

This film was heat-treated in a hot air drier maintained at a temperature of 170° C. for 3 minutes.

The heat-treated film obtained was soluble in water at temperatures not lower than 91° C. and had a 10% Young's modulus value of $5.1 \times 10^3$ kg/cm$^2$.

Bags of the type shown in FIG. 1 were made of this heat-treated single-layer film and evaluated for their performance characteristics.

COMPARATIVE EXAMPLE 2

The heat-treated film obtained in Comparative Example 1 was laminated on one side thereof with a 25-μm-thick low-density polyethylene film by means of an adhesive. Bags of the type shown in FIG. 1 were made of this laminate with the polyethylene film layer as the outside layer.

COMPARATIVE EXAMPLE 3

The heat-treated film obtained in Comparative Example 1 was provided on one side thereof with a 10-μm-thick polyvinylidene chloride coating layer, followed by further lamination of a nonwoven fabric having a weight of 20 g/cm$^2$ on the coating layer by means of an adhesive. Bags of the type shown in FIG. 1 were made of the resultant laminate with the nonwoven fabric layer as the outside layer.

COMPARATIVE EXAMPLE 4

The film not yet heat-treated as obtained in Comparative Example 1 was laminated on one side thereof with a 30-μm-thick etylene-vinyl acetate (ethylene content 70 mole percent) film and, on the other side, with a nonwoven fabric having a weight of 20 g/cm$^2$. Bags of the type shown in FIG. 1 were made of the resultant laminate with the nonwoven fabric layer as the outside layer.

COMPARATIVE EXAMPLE 5

Commercially available ostomy bags of a kind which has an ethylene-vinyl acetate copolymer (inside layer)/polyvinylidene chloride/ethylene-vinyl acetate copolymer (outside layer) three-layer structure were evaluated for performance characteristics.

COMPARATIVE EXAMPLE 6

The film not yet heat-treated as obtained in Comparative Example 1 was provided on one side thereof with a 15-μm-thick film layer of a 3-hydroxybutyrate copolymer containing 17 mole percent of hydroxybutyl valerate by applying a methylene chloride solution (containing o, p-toluenesulfonamide as a plasticizer in an amount of 20% by weight based on said copolymer). Bags of the type shown in FIG. 1 were made of the resultant laminate with the coating layer as the inside layer.

The evaluation results obtained with the bags of Examples 1 to 8 and Comparative Examples 1 to 6 are shown below in Table 1. The evaluation items and the evaluation criteria are as follows:

Evaluation items and criteria (1) Water resistance
○ : Good
X : Poor
(2) Odor barrier property (a: ammonia; b: trimethylamine; c: ethylmercaptan)
○ : No odor is perceivable.
Δ : Odor is perceivable slightly but there is no problem from the practical viewpoint.
X : Odor is too strong for the bags to be practicable.
(3) Non-sound-producing property or flexibility
○ : Very soft and flexible and good in non-sound-producing property.
Δ : Non-sound-producing but somewhat unsatisfactory in flexibility, or flexible but somewhat unsatisfactory in non-sound-producing property.
X : Poor in flexibility and in non-sound-producing property.
(4) Disposability in flush toilet
○ : No practical problem.
Δ : May cause some problem.
X : Undisposable.
(5) Feel and touch
⊙ : Very good
○ : Good Δ : Fair
X : Bad

TABLE 1

| | 1 | 2 a | 2 b | 2 c | 3 | 4 | 5 |
|---|---|---|---|---|---|---|---|
| Example 1 | ○ | Δ | ○ | Δ | ○ | ○ | ○ |
| Example 2 | ○ | Δ | ○ | ○ | ○ | ○ | Δ |
| Example 3 | ○ | Δ | ○ | ○ | ○ | ○ | ⊙ |
| Example 4 | ○ | Δ | ○ | ○ | ○ | ○ | ⊙ |
| Example 5 | ○ | Δ | ○ | Δ | ○ | ○ | ⊙ |
| Example 6 | ○ | Δ | ○ | ○ | ○ | ○ | ○ |
| Example 7 | ○ | Δ | ○ | Δ | ○ | ○ | ○ |
| Example 8 | ○ | Δ | ○ | ○ | ○ | ○ | ○ |
| Comparative Example 1 | ○ | Δ | Δ | Δ | x | x | Δ |
| Comparative Example 2 | ○ | Δ | ○ | Δ | x | x | x |
| Comparative Example 3 | ○ | Δ | ○ | Δ | x | x | Δ |
| Comparative Example 4 | x | x | ○ | x | Δ | Δ | Δ |
| Comparative Example 5 | ○ | Δ | ○ | Δ | x | x | Δ |
| Comparative Example 6 | ○ | Δ | ○ | x | Δ | Δx | |

What is claimed is:

1. A bag for the collection of waste material discharged from an artificial anus, said bag comprising an opening portion, a sealed portion and a multilayer packaging material, said multilayer packaging material consisting of at least three layers, wherein:
   (a) an inside layer consists of an oxyalkylene group-containing vinyl alcohol copolymer film layer which is soluble in water only at a temperature not lower than 55° C., having a 10% Young's modulus value of not more than $2 \times 10^3$ kg/cm² as measured at 20° C. and 50% relative humidity, and wherein the oxyalkylene group-containing vinyl alcohol copolymer has an oxyalkylene group content of 1–80 percent by weight;
   (b) a middle layer consists of a film layer of another polymer, and
   (c) an outside layer consists of a nonwoven fabric material.

2. A bag for the collection of waste material discharged from an artificial anus, said bag comprising an opening portion, a sealed portion and a multilayer packaging material, said multilayer packaging material consisting of at least three layers, wherein:
   (a) an outside layer consists of a nonwoven fabric;
   (b) a middle layer consists of an oxyalkylene group-containing vinyl alcohol copolymer film layer which is soluble in water only at a temperature not lower than 55° C., having a 10% Young's modulus value of not more than $2 \times 10^3$ kg/cm² as measured at 20° C. and 50% relative humidity, and wherein the oxyalkylene group-containing vinyl alcohol copolymer has an oxyalkylene group content of 1–80 percent by weight, and
   (c) an inside layer consists of a film layer of another polymer.

3. In a bag for the collection of waste material discharged from an artificial anus, said bag comprising an opening portion, a sealed portion and multilayer packaging material, wherein said multilayer packaging material consists of at least three layers, the improvement comprising the use of a multilayer packaging material consisting of:
   (a) an inside layer consisting of an oxyalkylene group-containing vinyl alcohol copolymer film layer which is soluble in water only at a temperature not lower than 55° C., having a 10% Young's modulus value of not more than $2 \times 10^3$ kg/cm² as measured at 20° C. and 50C. relative humidity, and wherein the oxyalkylene group-containing vinyl alcohol copolymer has an oxyalkylene group content of 1–80 percent by weight;
   (b) a middle layer consisting of a film layer of another polymer, and
   (c) an outside layer consisting of a nonwoven fabric material.

4. In a bag for the collection of waste material discharged from an artificial anus, said bag comprising an opening portion, a sealed portion and multilayer packaging material, and wherein said multilayer packaging material consist of at least three layers, the improvement comprising the use of a multilayer packaging material consisting of:
   (a) an outside layer consisting of a nonwoven fabric;
   (b) a middle layer consisting of an oxyalkylene group-containing vinyl alcohol copolymer film layer which is soluble in water only at a temperature not lower than 55° C., having a 10% Young's modulus value of not more than $2 \times 10^3$ kg/cm² as measured at 20° C. and 50% relative humidity, and wherein the oxyalkylene group-containing vinyl alcohol copolymer has an oxyalkylene group content of 1–80 percent by weight, and
   (c) an inside layer consisting of a film layer of another polymer.

* * * * *